(12) United States Patent
Siolek-Komorek et al.

(10) Patent No.: US 12,195,561 B2
(45) Date of Patent: Jan. 14, 2025

(54) BISSILYLAMINO-FUNCTIONALIZED CONJUGATED DIENES, THEIR PREPARATION AND THEIR USE IN THE PRODUCTION OF RUBBERS

(71) Applicants: SYNTHOS S.A., Oswiecim (PL); SYNTHOS DWORY 7 SPOLKA Z OGRANICZONA ODPOWIEDZIALNOSCIA SPOLKA JAWNA, Oswiecim (PL)

(72) Inventors: Maria Siolek-Komorek, Katowice (PL); Radoslaw Kozak, Chorzow (PL); Pawel Weda, Knurow (PL); Robert Bogacz, Bulowice (PL); Tomasz Skrok, Warsaw (PL); Malgorzata Pierog, Szczecin (PL)

(73) Assignees: SYNTHOS S.A., Oswiecim (PL); SYNTHOS DWORY 7 SPOLKA Z OGRANICZONA ODPOWIEDZIALNOSCIA, Oswiecim (PL)

( * ) Notice: Subject to any disclaimer, the term of this patent is extended or adjusted under 35 U.S.C. 154(b) by 792 days.

(21) Appl. No.: 17/425,164

(22) PCT Filed: Jan. 24, 2020

(86) PCT No.: PCT/EP2020/051760
§ 371 (c)(1),
(2) Date: Jul. 22, 2021

(87) PCT Pub. No.: WO2020/152332
PCT Pub. Date: Jul. 30, 2020

(65) Prior Publication Data
US 2022/0119555 A1 Apr. 21, 2022

(30) Foreign Application Priority Data
Jan. 24, 2019 (EP) .................................. 19153521

(51) Int. Cl.
| | | |
|---|---|---|
| *C08L 9/06* | (2006.01) | |
| *B60C 1/00* | (2006.01) | |
| *C07C 7/10* | (2006.01) | |
| *C07C 17/10* | (2006.01) | |
| *C08C 19/22* | (2006.01) | |
| *C08C 19/25* | (2006.01) | |
| *C08K 3/04* | (2006.01) | |

(Continued)

(52) U.S. Cl.
CPC ............ *C08C 19/22* (2013.01); *B60C 1/0016* (2013.01); *C07C 7/10* (2013.01); *C07C 17/10* (2013.01); *C08C 19/25* (2013.01); *C08K 3/04* (2013.01); *C08K 3/36* (2013.01); *C08K 5/098* (2013.01); *C08L 9/06* (2013.01); *C08L 2205/02* (2013.01); *C08L 2314/02* (2013.01)

(58) Field of Classification Search
CPC ....... C08F 226/02; C08F 126/02; C08F 26/02; C08L 15/00; C08L 9/00; C08K 3/36; C08K 3/04; C08K 5/18
See application file for complete search history.

(56) References Cited

U.S. PATENT DOCUMENTS

| | | | |
|---|---|---|---|
| 11,312,843 B2 | 4/2022 | Siolek-Komorek et al. | |
| 2011/0112212 A1 | 5/2011 | Kimura et al. | |

(Continued)

FOREIGN PATENT DOCUMENTS

| | | |
|---|---|---|
| CN | 102781968 A | 11/2012 |
| CN | 105026440 A | 11/2015 |

(Continued)

OTHER PUBLICATIONS

Leicht et al. Journal of the American Chemical Society 2017, 139, 6823-6826 (Year: 2017).*

(Continued)

*Primary Examiner* — Mark S Kaucher
(74) *Attorney, Agent, or Firm* — NIXON & VANDERHYE, PC

(57) ABSTRACT

The invention relates to bissilylamino-functionalized conjugated dienes, their preparation and their use in the production of rubbers. Further, the invention relates to rubbers and rubber compositions, and tires produced therefrom. The functionalized conjugated dienes are selected from the group of compounds of formula (Ia), (Ib), (Ic).

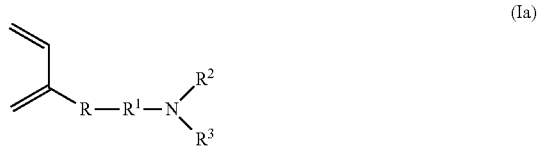

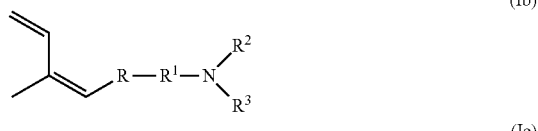

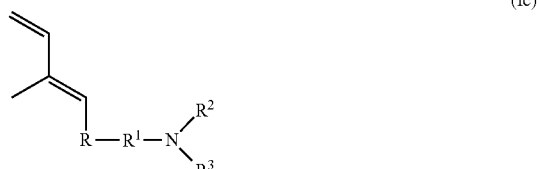

51 Claims, No Drawings

(51) Int. Cl.
*C08K 3/36* (2006.01)
*C08K 5/098* (2006.01)

(56) References Cited

U.S. PATENT DOCUMENTS

| | | |
|---|---|---|
| 2013/0331508 A1 | 12/2013 | Luo |
| 2014/0256847 A1 | 9/2014 | Sato |
| 2015/0118429 A1 | 4/2015 | Steinhauser et al. |
| 2018/0072821 A1 | 3/2018 | Janowski et al. |
| 2018/0291041 A1 | 10/2018 | Park et al. |
| 2019/0367708 A1 | 12/2019 | Siolek et al. |
| 2019/0375912 A1 | 12/2019 | Lee et al. |

FOREIGN PATENT DOCUMENTS

| | | | |
|---|---|---|---|
| CN | 108699181 | A | 10/2018 |
| CN | 101889050 | A | 11/2020 |
| DE | 25 21 652 | | 12/1975 |
| EP | 2 857 446 | | 4/2015 |
| EP | 3 064 546 | | 9/2016 |
| EP | 3 159 346 | | 4/2017 |
| GB | 1467751 | A | 3/1977 |
| JP | 62-283944 | | 12/1987 |
| JP | 2020508975 | | 3/2020 |
| JP | 2020510122 | | 4/2020 |
| RU | 2264414 | C1 | 11/2005 |
| RU | 2605250 | C2 | 4/2017 |
| RU | 2640041 | C2 | 12/2017 |
| RU | 2669799 | C2 | 10/2018 |
| WO | WO2015055252 | A1 | 4/2015 |
| WO | WO 2016/162473 | | 10/2016 |
| WO | WO 2016/162528 | | 10/2016 |
| WO | WO 2019/030059 | | 2/2019 |

OTHER PUBLICATIONS

Supporting information of Leicht et al. Journal of the American Chemical Society 2017, 139, 6823-6826 (Year: 2017).*

Schmalz et al., "Beitrag zur infrarotspektroskopischen Simultananalyse", Fresenius' Zeitschrift für analytische Chemie, Jan. 1961, 15 pages.

Friebe, et al., "Polymerization of 1,3-butadiene initiated by neodymium versatate/diisobutylaluminum hydride/ethylaluminum sesquichloride: Kinetics and conclusions about the reaction mechanism", Macromolecular Chemistry and Physics, 2002, 10 pages.

Leicht et al., "Synergetic Effect of Monomer Functional Group Coordination in Catalytic Insertion Polymerization", Journal of the American Chemical Society, vol. 139, No. 20, May 15, 2017, XP055440730, ISSN: 0002-7863, DOI: 10.1021/jacs.7b03087, 4 pages.

Friebe, et al., "A Comparison of Neodymium Versa-tate, Neodymium Neopentanolate and Neodymium Bis(2-ethylhexyl)phosphate in Ternary Ziegler Type Catalyst Systems With Regard to their Impact on the Polymerization of 1,3-Butadiene", Journal of Macromolecular Science, Part A: Pure and Applied Chemistry, 2005, 14 pages.

Kraft, "Struktur und Absorptionsspektroskopie der Kunststoffe", Verlag Chemie, Weinheim 1973, 24 pages.

Tavtorkin, et al., "Coordination Copolymerization of Butadiene with Polar Diene Monomers Based on Myrcene", Polymer Science, Series B, 2018, vol. 60, No. 6, 9 pages.

International Search Report issued in PCT/EP2020/051760 dated Apr. 6, 2020 (3 pages).

Written Opinion of International Searching Authority issued in PCT/EP2020/051760 dated Apr. 6, 2020 (6 pages).

* cited by examiner

BISSILYLAMINO-FUNCTIONALIZED CONJUGATED DIENES, THEIR PREPARATION AND THEIR USE IN THE PRODUCTION OF RUBBERS

The present invention relates to bissilylamino-functionalized conjugated dienes, their preparation and their use in the production of rubbers. Further, the invention relates to rubbers and rubber compositions, and tires produced therefrom.

A variety of conjugated diene monomers is known that can be used in the production of synthetic rubbers. However, there is a need in the art for further conjugated diene monomers that can be used in advantageous polymerization processes, or that confer advantageous properties to the rubbers produced from such conjugated diene monomers.

EP 3 159 346 A1 teaches aminosilane-functionalized diene compounds that are useful as modifying monomers in the polymerization of conjugated diene monomers, optionally together with aromatic vinyl monomers, thus producing polymers, specifically elastomeric polymers, which can be used in rubber articles such as tires.

WO2016/162473 A1 and WO2016/162528 A1 disclose aminosilyl-functionalized styrenes and methods for their preparation, as well as the use of the styrene derivatives in the preparation of copolymers thereof.

EP 3 064 546 A1 teaches the use of vinylsilanes in the production of rubbers. EP 2 857 446 A1 teaches a conjugated diene polymer derived from conjugated diene, a monomer unit $V^1$-$S^1$, and a monomer unit $V^2$-$A^2$, where $V^1$ and $V^2$ each represent a hydrocarbyl group containing a polymerizable carbon-carbon double bond, $S^1$ represents a substituted silyl group, and A2 is an amino group or a nitrogen-containing heterocycle group.

Leicht et al., JACS 2017, 139, 6823-6826 report on the behaviour of sulphur- and nitrogen-functionalized alkyl dienes under Ziegler-Natta conditions.

Tavtorkin et al. (Polymer Science, Series B 2018, Volume 60, No. 6, pages 699-707) disclose myrcene-based monomers.

It was an object of the invention to provide conjugated diene monomers for the production of synthetic rubbers. These conjugated diene monomers should be based on easily accessible starting materials, and should be accessible via simple synthetic routes. Moreover, the conjugated diene monomers should be universally applicable, i.e. in a variety of different polymerization processes, and should confer advantageous properties to the rubbers, rubber compositions, and tires produced therefrom.

It has now surprisingly been found in accordance with the present invention that this object is solved by the use of specific conjugated dienes having bissilylamino functionalization. The functionalized conjugated dienes of the invention are selected from the group of compounds of formulae (Ia), (Ib), (Ic)

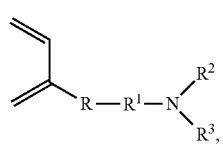
(Ia)

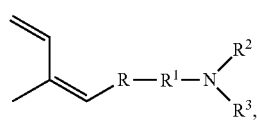
(Ib)

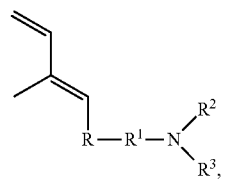
(Ic)

wherein
R is a branched, unsaturated hydrocarbylene group, and the starting conjugated diene selected from the group of compounds of formula (IIa), (IIb), (IIc)

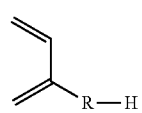
(IIa)

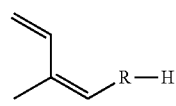
(IIb)

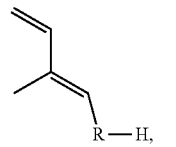
(IIc)

from which the functionalized conjugated diene of formula (Ia), (Ib), (Ic) is derived, has at least 10 carbon atoms, $R^1$ is selected from
 i) a single bond,
 ii) one or more of an oxygen atom, a sulfur atom, and a group $NR^4$; and
 iii) an organylene group optionally containing one or more selected from an oxygen atom, a sulfur atom, and a group $NR^4$;

$R^2$ and $R^3$ can be the same or different and represent $Si(R^5)_3$, wherein each $R^5$ can be the same or different and represents an organyl group optionally containing one or more heteroatoms selected from an oxygen atom, a sulfur atom, a nitrogen atom, and a silicon atom;

$R^4$ represents an organyl group optionally containing one or more heteroatoms selected from an oxygen atom, a sulfur atom, a nitrogen atom, and a silicon atom.

These functionalized conjugated dienes are preferably used as comonomers in the production of elastomeric copolymers. Alternatively, or additionally, they are preferably used in the preparation of polymerization initiators. When the functionalized conjugated dienes of the invention are incorporated into the elastomeric copolymer, as initiator and/or as comonomer, incorporation of additional functionalized comonomer, and/or omega functionalization, can be reduced, or can even completely be dispensed with.

The functionalized conjugated dienes of the invention, when used e.g. in the production of solution styrene butadiene rubber (S-SBR) and Ziegler-Natta catalyzed (e.g. neodymium) butadiene rubber (Nd-BR), increase the interaction of the polymer with fillers and thus filler dispersion in the polymer matrix, helping to improve the dynamic and mechanical properties of tire tread compounds. The functionalized conjugated dienes of the invention may be synthesized from easily-accessible starting material, by simple synthetic methods. This is in contrast to the teaching of EP 3 159 346 A1, which relies on a synthetic method involving chloroprene as starting material. However, chloroprene is a highly volatile and flammable chemical. In contrast to the functionalized alkyl dienes of Leicht et al. (JACS 2017, 139, 6823-6826), the functionalized conjugated dienes of the invention have unsaturation in group R, such as a double bond, which unsaturation can play a crucial role in the vulcanization stage, to give better application results (especially better mechanical properties). Also, and in contrast to the myrcene-based monomers disclosed in Tavtorkin et al. (Polymer Science, Series B 2018, Volume 60, No. 6, pages 699-707), the functionalized conjugated dienes of the invention show an improved interaction with silica, by virtue of the silyl groups ($R^2$, $R^3$).

In a first aspect, the present invention relates to methods for the preparation of a functionalized conjugated diene.

In a second aspect, the invention relates to the functionalized conjugated diene.

In a third aspect, the invention relates to the use of the functionalized conjugated dienes in the production of an elastomeric copolymer.

In a fourth aspect, the invention relates to a process for the production of copolymer component comprising coupled copolymer and terminally modified copolymer.

In a fifth aspect, the invention relates to a process for producing an elastomeric copolymer comprising anionic polymerization conditions.

In a sixth aspect, the invention relates to a process for producing an elastomeric copolymer comprising Ziegler-Natta polymerization conditions.

In a seventh aspect, the invention relates to an elastomeric copolymer.

In an eighth aspect, the invention relates to a method for producing a rubber.

In a ninth aspect, the invention relates to a rubber.

In a tenth aspect, the invention relates to a rubber composition.

In an eleventh aspect, the invention relates to a tire component.

Finally, in a twelfth aspect, the invention relates to a tire.

DETAILED DESCRIPTION OF THE INVENTION

In the first aspect, the invention relates to a method for the preparation of a functionalized conjugated diene selected from the group of compounds of formula (Ia), (Ib), (Ic)

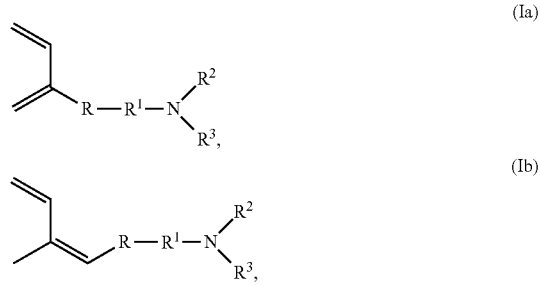

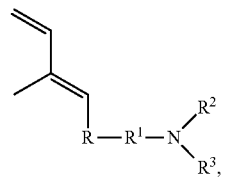

wherein
R is a branched, unsaturated hydrocarbylene group, and the starting conjugated diene selected from the group of compounds of formula (IIa), (IIb), (IIc)

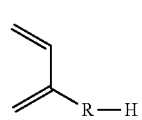

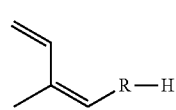

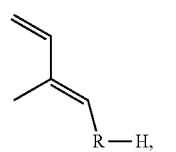

from which the functionalized conjugated diene of formula (Ia), (Ib), (Ic) is derived, has at least 10 carbon atoms,
$R^1$ is selected from
i) a single bond,
ii) one or more of an oxygen atom, a sulfur atom, and a group $NR^4$; and
iii) an organylene group optionally containing one or more selected from an oxygen atom, a sulfur atom, and a group $NR^4$;
$R^2$ and $R^3$ can be the same or different and represent $Si(R^5)_3$, wherein each $R^5$ can be the same or different and represents an organyl group optionally containing one or more heteroatoms selected from an oxygen atom, a sulfur atom, a nitrogen atom, and a silicon atom;
$R^4$ represents an organyl group optionally containing one or more heteroatoms selected from an oxygen atom, a sulfur atom, a nitrogen atom, and a silicon atom;
the method comprising
reacting a conjugated diene halide selected from the group of compounds of formula (IIIa), (IIIb), (IIIc)

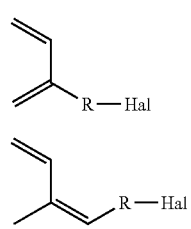

-continued

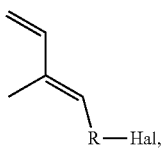
(IIc)

wherein Hal is selected from fluorine, chlorine, bromine, and iodine atoms, and Hal is preferably a chlorine atom, with an amide of formula (IV)

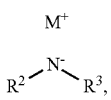
(IV)

wherein M is an alkali metal selected from lithium, sodium, and potassium, and M is preferably sodium.

The preparation of the conjugated diene halide intermediate of formula (IIIa), (IIIb), (IIIc) wherein $Y^1$ is a chlorine atom may be performed using a chlorinating agent comprising trichloroisocyanuric acid, dichloroisocyanuric acid, an alkali metal salt of dichloroisocyanuric acid, or a mixture thereof. Further details regarding the synthesis of this conjugated diene chloride intermediate of formula (IIIa), (IIIb), (IIIc) are given in WO 2019/030059 A1, which is hereby incorporated by reference herein in its entirety.

The functionalized conjugated diene of the second aspect of the invention is selected from the group of compounds of formula (Ia), (Ib), (Ic)

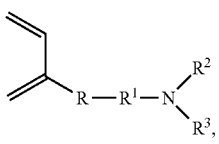
(Ia)

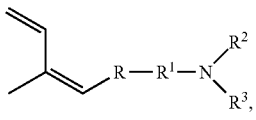
(Ib)

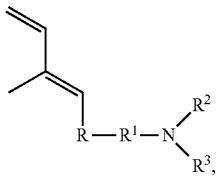
(Ic)

wherein
R is a branched, unsaturated hydrocarbylene group, and the starting conjugated diene selected from the group of compounds of formula (IIa), (IIb), (IIc)

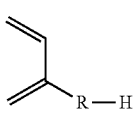
(IIa)

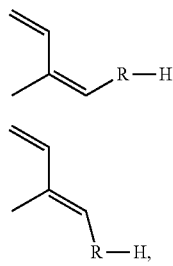
(IIb)

(IIc)

from which the functionalized conjugated diene of formula (Ia), (Ib), (Ic) is derived, has at least 10 carbon atoms, $R^1$ is selected from
i) a single bond,
ii) one or more of an oxygen atom, a sulfur atom, and a group $NR^4$; and
iii) an organylene group optionally containing one or more selected from an oxygen atom, a sulfur atom, and a group $NR^4$;

$R^2$ and $R^3$ can be the same or different and represent $Si(R^5)_3$, wherein each $R^5$ can be the same or different and represents an organyl group optionally containing one or more heteroatoms selected from an oxygen atom, a sulfur atom, a nitrogen atom, and a silicon atom;

$R^4$ represents an organyl group optionally containing one or more heteroatoms selected from an oxygen atom, a sulfur atom, a nitrogen atom, and a silicon atom.

In the description of the present invention, an organyl group is any organic substituent group, regardless of functional type, having one free valence at a carbon atom. Preferably, an organyl group contains from 1 to 10 carbon atoms, and optionally one or more heteroatoms selected from an oxygen atom, a sulfur atom, and a nitrogen atom, and, if applicable, a silicon atom; or, in the case of an aryl, heteroaryl or aralkyl group, contains from 6 to 10 carbon atoms, and optionally one or more heteroatoms selected from an oxygen atom, a sulfur atom, and a nitrogen atom, and, if applicable, a silicon atom.

Also, an organylene group is any organic substituent group, regardless of functional type, having two free valences at one carbon atom, or one free valence at each of two carbon atoms thereof. Preferably, an organylene group contains from 1 to 10 carbon atoms, and optionally one or more heteroatoms selected from an oxygen atom, a sulfur atom, and a nitrogen atom, and, if applicable, a silicon atom; or, in the case of an arylene, heteroarylene or aralkylene group, contains from 6 to 10 carbon atoms, and optionally one or more heteroatoms selected from an oxygen atom, a sulfur atom, and a nitrogen atom, and, if applicable, a silicon atom.

Preferably, $R^1$ of the functionalized conjugated diene of the present invention is i) a single bond.

According to the invention, R is a branched, unsaturated hydrocarbylene group. More preferably, the starting conjugated diene of formula (IIa), (IIb), (IIc) is selected from terpenes and 4,8-dimethyl-1,3,7-nonatriene. In particular, the terpene is selected from myrcene and ocimene. For instance, the terpene is myrcene selected from α-myrcene and β-myrcene.

It is preferred that the terpene starting material of formula (IIa), (IIb), (IIc) for the preparation of the functionalized conjugated diene of formula (Ia), (Ib), (Ic) is selected from monoterpenes, sesquiterpenes, and diterpenes. Preferably, the terpene is a monoterpene, such as myrcene or ocimene. In particular, the myrcene starting material for the method according to the first aspect is selected from α-myrcene and β-myrcene, most preferably, the myrcene is β-myrcene.

Monoterpenes are dimers of isoprenoid precursors, and myrcene is one of the most important ones because it is a relevant precursor to many terpenes. Myrcene is a monoterpene with a highly active diene structure. It is used in a variety of industrial processes. For example, the technical syntheses of flavors such as menthol, geraniol, nerol, and linalool typically start from myrcene. Also, myrcene is a relatively inexpensive and environmentally friendly starting material.

Examples for the starting conjugated dienes are the following monoterpenes: myrcenes, or 3,7-dimethyl-1,3,7-octatriene ((E)-α-ocimene), (Z)-3,7-dimethyl-1,3,6-octatriene ((Z)-β-ocimene), (E)-3,7-dimethyl-1,3,6-octatriene ((E)-β-ocimene), or 2,6-dimethyl-2,4,6-octatriene (allo-ocimene).

Alternatively, 4,8-dimethyl-1,3,7-nonatriene is used as a starting conjugated diene. For example, and most preferred, the functionalized conjugated diene of the invention is a myrcene derivative of formula (Ia1), (Ib1), or (Ic1)

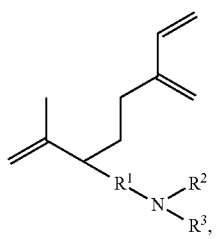
(Ia1)

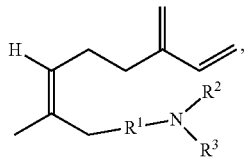
(Ib1)

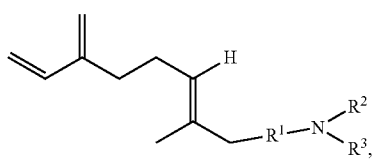
(Ic1)

In a preferred embodiment, $R^2$ and $R^3$ are the same, wherein each $R^5$ in the respective group $Si(R^5)_3$ can be the same or different and represents an organyl group optionally containing one or more heteroatoms selected from an oxygen atom, a sulfur atom, a nitrogen atom, and a silicon atom. More preferably, each $R^5$ in the respective group $Si(R^5)_3$ is the same and represents a linear or branched, saturated or unsaturated hydrocarbyl group, most preferably, each $R^5$ is the same and represents a linear or branched alkyl, aryl, or alkaryl group, in particular, each $R^5$ is the same and represents $CH_3$ or $C_6H_5$. It is most preferred that each $R^5$ is $CH_3$, i.e. $R^2$ and $R^3$ are each $SiMe_3$.

Consequently, the myrcene derivative according to the invention is most preferably of formula (Ia2), (Ib2), or (Ic2)

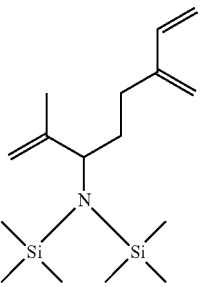
(Ia2)

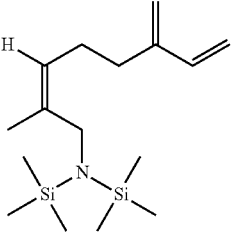
(Ia2)

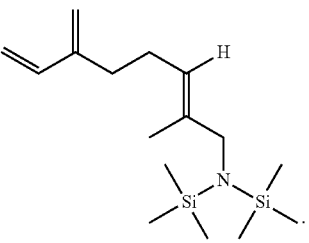
(Ic2)

In a third aspect, the present invention relates to the use of one or more functionalized conjugated dienes of the second aspect in the production of an elastomeric copolymer.

The elastomeric copolymer preferably comprises, in addition to one or more units derived from the one or more functionalized conjugated dienes selected from the group of compounds of formula (Ia), (Ib), (Ic), units derived from one or more conjugated diene monomers.

The conjugated diene monomer as used in the production of the elastomeric copolymer according to the third aspect of the invention is preferably selected from 1,3-butadiene, isoprene, 1,3-pentadiene, 2,3-dimethyl-1,3-butadiene, 2-methyl-1,3-pentadiene, 2,3-dimethyl-1,3-pentadiene, 2-phenyl-1,3-butadiene, and 4,5-diethyl-1,3-octadiene. More preferably, the conjugated diene monomer is selected from 1,3-butadiene and isoprene, in particular, the conjugated diene monomer is 1,3-butadiene.

Preferably, the use according to the third aspect is in the production of an elastomeric copolymer by 1) anionic polymerization or by 2) coordination polymerization.

It is preferred that the elastomeric copolymer further comprises units derived from one or more vinyl aromatic monomers. The vinyl aromatic monomer is preferably selected from styrene, 1-vinylnaphthalene, 3-methyl styrene, 3,5-diethylstyrene, 4-propylstyrene, 2,4,6-trimethylstyrene, 4-dodecylstyrene, 3-methyl-5-n-hexylstyrene, 4-phenylstyrene, 2-ethyl-4-benzylstyrene, 3,5-diphenylstyrene, 2,3,4,5-tetraethylstyrene, 3-ethyl-1-vinylnaphthalene, 6-isopropyl-1-vinylnaphthalene, 6-cyclohexyl-1-vinylnaphthalene, 7-dodecyl-2-vinylnaphthalene, and α-methyl styrene. More preferably, the vinyl aromatic monomer is selected from styrene, 3-methylstyrene, and α-methylstyrene. In particular, the vinyl aromatic monomer is styrene.

According to the invention, the amount of units derived from the one or more functionalized conjugated dienes selected from of the group of compounds of formula (Ia), (Ib), (Ic) is preferably in a range of from 0.05 to 5 wt. %, more preferably in a range of from 0.1 to 1.5 wt. %, most preferably in a range of from 0.2 to 0.8 wt. %, e.g. in a range of from 0.2 to 0.6 wt. %, such as about 0.5 wt. %, each based on the weight of the elastomeric copolymer.

The use according to the third aspect may be of an alkali metal salt derivative of the functionalized conjugated diene selected from the group of compounds of formula (Ia), (Ib), (Ic), as initiator for the anionic copolymerization of one or more conjugated diene monomers, optionally one or more vinyl aromatic monomers, and optionally one or more functionalized conjugated dienes selected from the group of compounds of formula (Ia), (Ib), (Ic).

In a fourth aspect, the invention relates to a process for the production of a copolymer component comprising coupled copolymer and terminally modified copolymer, the process comprising the following steps:
(1) providing an initiator component, wherein the initiator component optionally comprises one or more alkali metal salt derivatives of a one or more functionalized conjugated dienes selected from the group of compounds of formula (Ia), (Ib), (Ic),
(2) contacting a monomer component comprising
   i) optionally one or more functionalized conjugated dienes selected from the group of compounds of formula (Ia), (Ib), (Ic),
   ii) one or more conjugated diene monomers and
   iii) optionally one or more vinyl aromatic monomers, with the initiator component, to initiate anionic copolymerization;
(3) continuing copolymerization, to result in a copolymer;
(4) optionally continuing copolymerization of the copolymer, in the presence of one or more functionalized monomers, to result in a functionalized copolymer;
(5) optionally coupling a part of the copolymer of step (3) or the functionalized copolymer of step (4) with one or more coupling agents, to result in coupled copolymer;
(6) optionally terminally modifying a part of the copolymer of step (3) or the functionalized copolymer of step (4) with one or more terminal modifying agents, to result in terminally modified copolymer;
(7) optionally post-polymerization modification of the copolymer of step (3), or the functionalized copolymer of step (4), or the coupled copolymer of step (5), or the terminally modified copolymer of step (6), by
   a. re-initiating with an initiator component to initiate anionic copolymerization, and
   b. continuing copolymerization, in the presence of one or more functionalized monomers, preferably one or more functionalized conjugated dienes selected from the group of compounds of formula (Ia), (Ib), (Ic), to result in copolymer with functionalized side-groups.

The functionalized conjugated diene selected from the group of compounds of formula (Ia), (Ib), (Ic) is used in at least one of steps (1) and (2).

In a fifth aspect, the invention relates to a process for producing an elastomeric copolymer comprising subjecting
   i) one or more functionalized conjugated dienes selected from the group of compounds of formula (Ia), (Ib), (Ic),
   ii) one or more conjugated diene monomers, and
   iii) optionally one or more vinyl aromatic monomers to anionic polymerization conditions. Preferably, the anionic polymerization conditions include initiating the polymerization with an alkali metal salt derivative of the one or more functionalized conjugated dienes of formula (Ia), (Ib), (Ic), wherein the alkali metal is selected from lithium, sodium, and potassium.

The polymerization will typically be initiated with an anionic initiator, such as organic lithium compound, a lithium amide compound, or a functionalized initiator-containing nitrogen atom. As the organic lithium compound, there are preferred those having a hydrocarbon group having 1 to 20 carbon atoms. There can be mentioned, for example, methyl lithium, ethyl lithium, n-propyl lithium, isopropyl lithium, n-butyl lithium, sec-butyl lithium, tert-octyl lithium, n-decyl lithium, phenyllithium, 2-naphthyl lithium, 2-butylphenyl lithium, 4-phenylbutyl lithium, cyclohexyl lithium, cyclopentyl lithium, and a reaction product of diisopropenylbenzene with butyl lithium. Of these compounds, n-butyl lithium and sec-butyl lithium are preferred.

As the lithium amide compound, there can be mentioned, for example, lithium hexamethyleneimide, lithium pyrrolidide, lithium piperidide, lithium heptamethyleneimide, lithium dodecamethyleneimide, lithium dimethylamide, lithium diethylamide, lithium dibutylamide, lithium dipropylamide, lithium diheptylamide, lithium dihexylamide, lithium dioctylamide, lithium di-2-ethylhexylamide, lithium didecylamide, lithium N-methylpiperadide, lithium ethylpropylamide, lithium ethylbutylamide, lithium ethylbenzylamide and lithium methylphenethylamide. Of these compounds, preferred from the standpoint of the polymerization initiation ability are cyclic lithium amides such as lithium hexamethyleneimide, lithium pyrrolidide, lithium piperidide, lithium heptamethyleneimide and lithium dodecamethyleneimide; and particularly preferred are lithium hexamethyleneimide, lithium pyrrolidide and lithium piperidide.

The lithium amide compound, if present, is, in general, prepared beforehand from a secondary amine and a lithium compound and then used in polymerization; however, it may be prepared in the polymerization system (in situ). The amount of the lithium initiator utilized will vary with the monomers being polymerized and with the molecular weight that is desired for the polymer being synthesized.

Functionalized initiator is preferably prepared by the reaction of an organometallic compound, namely a salt of an alkali metal, such as n-butyl lithium, with a functionalized conjugated diene selected from the group of compounds of formula (Ia), (Ib), (Ic).

Using anionic polymerization, copolymers having a linear structure or a star structure may be obtained. Also, branching may be performed with e.g. divinylbenzene. The branching level is difficult to predict since it is difficult to fractionate the specific polymer fractions.

Thus, it is more appropriate to define the copolymers as obtained by anionic polymerization by their dispersity index, $M_w/M_n$, which is typically as follows:
Linear copolymer: 1.01 to 2.0;
Coupled copolymer: 1.1 to 3; and
Branched copolymer: 1.1 to 8.0.

According to the sixth aspect, the invention relates to a process for producing an elastomeric copolymer comprising subjecting
   i) one or more functionalized conjugated dienes selected from the group of compounds of formula (Ia), (Ib), (Ic) and
   ii) one or more conjugated diene monomers
to Ziegler-Natta polymerization conditions.

In the coordination polymerization of conjugated diene (such as 1,3-butadiene), a Ziegler-Natta catalyst is used. Typical catalyst compositions are binary, ternary, or quaternary systems. Binary systems comprise catalytic metal chloride (e.g. chloride of Ni, Co, Ti, Nd, V, Ti, Zr, or Fe) and co-catalyst (e.g. aluminum alkyl or a magnesium alkyl compound). In ternary catalyst systems, a halide-free metal precursor (such as neodymium phosphate) is combined with a co-catalyst (such as aluminium or magnesium alkyl) and a halide donor. Adding halide donors to halide-free catalyst systems significantly increases catalyst activities and cis-1,4 or trans-1,4 contents. In quaternary catalyst systems, a solubilizing agent for either the metal-salt or for the halide donor is used, in addition to the components as used in ternary systems.

The Ziegler-Natta polymerization conditions consequently preferably include a catalyst system comprising 1) metal chloride and 2) co-catalyst. More preferably, the metal chloride 1) is selected from chlorides of one or more of Ni, Co, Ti, Nd, V, Ti, Zr, and Fe, and the co-catalyst 2) is selected from one or more of aluminium and magnesium alkyl compounds. Also, the Ziegler-Natta polymerization conditions may include the presence of further monomers.

It is alternatively preferred that the Ziegler-Natta polymerization conditions include a catalyst system comprising 1) non-halide metal compound, 2) co-catalyst, and 3) halide donor compound. The non-halide metal compound 1) is preferably one or more Nd compounds; more preferably the Nd compound is selected from neodymium carboxylates, neodymium alcoholates, neodymium phosphates, neodymium phosphonates, neodymium allyl compounds, neodymium cyclopentadienyl complexes, neodymium amides, and neodymium acetylacetonates.

The most effective catalysts for the production of high cis polybutadiene are ternary systems based on neodymium, where catalyst precursors such as 1) neodymium carboxylates (e.g. neodymium(III) versatate (NdV), neodymium(III) octanoate (NdO), neodymium(III) iso-octanoate (NdiO), neodymium(III) naphthenate (NdN); 2) neodymium alcoholates (e.g. $Nd(OBu)_3$, $Nd(OiPr)_3$); 3) neodymium phosphates and phosphonates (e.g. neodymium bis(2-ethylhexyl) phosphate (NdP), bis(2-ethylhexanol)phosphonate); 4) neodymium allyl compounds; 5) neodymium cyclopentadienyl complexes (e.g. monocyclopentadienyl neodymium dichloride ($CpNdCl_2$), monocyclopentadienyl dialkyl neodymium ($CpNdR_2$), monocyclopentadienyl diallyl neodymium ($CpNd(\eta_3-C_3H_5)_2$), salts of monoclopentadienyl tris allyl neodymium (e.g $Li[CpNd(\eta_3-C_3H_5)_3]$), dicyclopentadienyl neodymium monochloride ($Cp_2NdCl$), dicyclopentadienyl monoalkyl neodymium ($Cp_2NdR$), silylene-bridged dicyclopentadienyl neodymium derivatives (e.g. $[R_2Si(Cp)_2]Nd(Cl/R)$); 6) neodymium amides (e.g. $Nd(N(SiMe_3)_2)_3$); or 7) neodymium acetylacetonates are used, in combination with one or more co-catalyst such as: $AlMe_3$ (TMA), $AlEt_3$ (TEA), $AlBu_3$ (TIBA), $AlOct_3$, methyl alumoxane (MAO), tetraisobutyl dialumoxane (TIBAO), $B(C_6F_5)_3$, modified methyl alumoxane (MMAO), hexaisobutylalumoxane (HIBAO), diisobutylaluminum hydride (DIBAH), $MgR_2$, $AlPr_3$, $AlBu_3$, $AlHex_3$, $AlOct_3$, $AlDodec_3$, $AlEt_3$, or $AlMe_3$.

Examples for halide donors are $SiCl_4$, ethylaluminium sesquichloride (EASC), diethylaluminium chloride (DEAC), dimethylaluminium chloride, butyl chloride (BuCl), dibutylaluminium chloride, $AlBr_3$, $EtAlCl_2$, and $Me_3SiCl$.

The copolymer as produced in accordance with the sixth aspect, i.e. by coordination polymerization, preferably has linear structure or branched structure. The polymer structure is dictated by catalyst composition and is typically as follows ($M_w/M_n$):

Linear copolymer: 1.5 to 5.0,
Branched copolymer: 1.5 to 20.0.

According to the seventh aspect, the invention relates to an elastomeric copolymer comprising repeat units that are derived from
A) 0.05 wt. % to 5 wt. %, by weight of the copolymer, of one or more functionalized conjugated dienes selected from the group of compounds of formula (Ia), (Ib), (Ic);
B) 45 wt. % to 99.95 wt. %, by weight of the copolymer, of one or more conjugated diene monomers;
C) 0 wt. % to 50 wt. %, by weight of the copolymer, of one or more vinyl aromatic monomers.

The amount of B) conjugated diene monomer in the elastomeric copolymer of the seventh aspect is preferably 50 to 92 wt. %, by weight of the copolymer, more preferably 60 to 90 wt. %, by weight of the copolymer, in particular 65 to 80 wt. %, by weight of the copolymer.

The vinyl aromatic monomer, when present, is preferably selected from styrene, 1-vinylnaphthalene, 3-methylstyrene, 3,5-diethylstyrene, 4-propylstyrene, 2,4,6-trimethylstyrene, 4-dodecylstyrene, 3-methyl-5-n-hexylstyrene, 4-phenylstyrene, 2-ethyl-4-benzylstyrene, 3,5-diphenylstyrene, 2,3,4,5-tetraethylstyrene, 3-ethyl-1-vinylnaphthalene, 6-isopropyl-1-vinylnaphthalene, 6-cyclohexyl-1-vinylnaphthalene, 7-dodecyl-2-vinylnaphthalene, and α-methylstyrene. More preferably, the vinyl aromatic monomer is selected from styrene, 3-methylstyrene and α-methylstyrene. In particular, the vinyl aromatic monomer is styrene.

The amount of C) vinyl aromatic monomer in the elastomeric copolymer according to the seventh aspect of the present invention is preferably 8 to 45 wt. %, by weight of the copolymer, more preferably 10 to 40 wt. %, by weight of the copolymer, in particular 20 to 35 wt. %, by weight of the copolymer.

Alternatively, the elastomeric copolymer comprises less than 1 wt. % C) vinyl aromatic monomer (and preferably no C) vinyl aromatic monomer), and the amount of B) conjugated diene monomer is 95 to 99.95 wt. %, by weight of the copolymer, preferably 98 to 99.6 wt. %, by weight of the copolymer, in particular 99.0 to 99.4 wt. %, by weight of the copolymer.

The conjugated diene monomer in the elastomeric copolymer according to the seventh aspect is preferably selected from 1,3-butadiene, isoprene, 1,3-pentadiene, 2,3-dimethyl-1,3-butadiene, 2-methyl-1,3-pentadiene, 2,3-dimethyl-1,3-pentadiene, 2-phenyl-1,3-butadiene, and 4,5-diethyl-1,3-octadiene. More preferably, the conjugated diene monomer is selected from 1,3-butadiene and isoprene. The conjugated diene monomer is in particular 1,3-butadiene.

The elastomeric copolymer according to the invention may comprise units having a linear structure.

Also, the copolymer may comprise units having a branched structure.

Moreover, the elastomeric copolymer may comprise units having a star structure and being produced by the reaction of metal-terminated living linear copolymer with one or more coupling agents in anionic polymerization conditions. The coupling agent may be
I) a tin halide coupling agent (preferably the tin halide coupling agent is tin tetrachloride),
or
II) a silicon halide coupling agent (preferably the silicon halide coupling agent is selected from silicon tetrachloride, silicon tetrabromide, silicon tetrafluoride, silicon tetraiodide, hexachlorodisilane, hexabromodisilane, hexafluorodisilane, hexaiododisilane, octachlorotrisilane, octabromotrisilane, octafluorotrisilane, octaiodotrisilane, hexachlorodisiloxane, 2,2,4,4,6,6-hexachloro-2,4,6-trisilaheptane-1,2,3,4,5,6-hexakis[2-(methyldichlorosilyl)ethyl]benzene, and alkyl silicon halides of general formula (V)

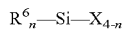

wherein $R^6$ is a monovalent aliphatic hydrocarbon group having 1 to 20 carbon atoms or a monovalent aromatic hydrocarbon group having 6 to 18 carbon atoms; n is an integer of 1 to 2; and X can be a chlorine, bromine, fluorine or iodine atom).

In the elastomeric copolymer according to the seventh aspect, the fraction of units having star structure is preferably between 0 and 75%, by weight of the copolymer.

According to the eighth aspect, the invention relates to a method for producing a rubber comprising vulcanizing the elastomeric copolymer according to the seventh aspect in the presence of one or more vulcanizing agents.

According to a ninth aspect, the invention relates to a rubber as obtainable according to the method of the eighth aspect.

According to a tenth aspect, the invention relates to a rubber composition comprising x) a rubber component comprising the rubber according to the ninth aspect. Preferably, the rubber composition further comprises y) one or more fillers. The filler is preferably selected from the group consisting of silica and carbon black. Most preferably, the rubber composition comprises y) both silica and carbon black.

In a preferred embodiment of the tenth aspect, the amount of filler component y) in the rubber composition is 10 to 150 parts by mass relative to 100 parts by mass of the rubber component x) (phr). Preferably, the amount of filler component y) is 20 to 140 phr. More preferably, the amount of filler component y) is 30 to 130 phr.

Preferably, the rubber component x) in the rubber composition according to the tenth aspect additionally comprises one or more further rubbery polymers. It is preferred that the further rubbery polymer is selected from the group consisting of natural rubber, synthetic isoprene rubber, butadiene rubber, styrene-butadiene rubber, ethylene-α-olefin copolymer rubber, ethylene-α-olefin-diene copolymer rubber, acrylonitrile-butadiene copolymer rubber, chloroprene rubber and halogenated butyl rubber.

The tire component according to the eleventh aspect of the invention comprises the rubber composition according to the tenth aspect. Preferably, the tire component is a tire tread.

The tire according to the twelfth aspect of the invention comprises the tire component of the eleventh aspect.

The advantages of the present invention become more apparent from the following examples. Unless indicated otherwise, all percentages are given by weight.

EXAMPLES

The starting material, chloromyrcene, was prepared in accordance with WO 2019/030059 A1, from beta-myrcene (7-methyl-3-methylene-1,6-octadiene), to give a product which is a mixture of three isomers, which mixture contains more than 95% of 3-chloro-2-methyl-6-methylene-1,7-octadiene

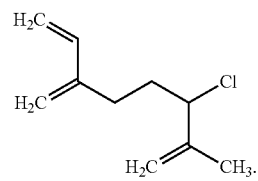

1. Synthesis of Monomers: Example 1a

A reactor of 1 L capacity, equipped with a magnetic stirrer, a dropping funnel and a reflux condenser equipped with a gas introduction attachment and an oil valve (Zaitsev washer), was in an argon atmosphere loaded with chloromyrcene (namely the mixture as described above, 150 g, 0.88 mol) followed by the addition of dry and deoxygenated tetrahydrofuran (THF, 200 mL). This was done at room temperature, with stirring of the reactor contents. Then, the dropping funnel was filled with 402.9 g of sodium bis(trimethylsilyl)amide 40% solution in THF (0.88 mol, 161.5 g of pure sodium bis(trimethylsilyl)amide). The sodium bis(trimethylsilyl)amide solution was added dropwise to the reaction, keeping the reaction temperature under 30° C. After the dosing of sodium bis(trimethylsilyl)amide solution was completed, the reactor temperature was maintained in the range of 30° C. for one hour, followed by cooling to room temperature. Then, the solvent was evaporated from the postreaction mixture under reduced pressure, and 1.0 L of n-hexane were added to the reaction residue. The obtained suspension was filtered off and the precipitate was washed with three portions of n-hexane of 200 mL each. Then, the solvent was evaporated from the obtained filtrate under reduced pressure at 40° C. until a constant pressure was achieved 252 g of product were obtained, with a yield of 80%.

GC-MS: 295 (1.69), 280 (6.59), 174 (22.46), 134 (1.58), 100 (9.18), 86 (6.55), 73 (100.00), 59 (18.51), 45 (12.56)

II. Synthetic Examples for Functionalized Rubbers

II.1 Application of Functionalized Myrcene in Anionic Polymerization

In order to provide more details about the synthesis and properties of elastomers produced according to the present invention, functionalized styrene-butadiene copolymers with exactly controlled micro- and macrostructure and with functional groups are described in Examples 2b, 3b and 4b below, and are compared with a non-functionalized copolymer as described in Comparative Example 1b.
Polymerization
Inertization Step:

Cyclohexane (1.2 kg) was added to a nitrogen-purged two-liter reactor and treated with 1 gram of 1.6 M n-butyllithium solution in cyclohexane. The solution was heated to 70° C. and vigorously stirred for 10 minutes, to perform cleaning and inertization of the reactor. After that, solvent was removed via a drain valve and nitrogen was purged again.

Example 1 b (Comparative)

Cyclohexane (820 g) was added to the inerted two-liter reactor, followed by addition of styrene (31 g) and of 1,3-butadiene (117 g). Inhibitor from styrene and 1,3-butadiene was removed. Next, tetramethylethylenediamine (TMEDA, 2.21 mmol) was added, to provide random incorporation of styrene monomer and to increase vinyl content, from the butadiene-derived units. The solution inside the reactor was heated to 60° C. and continuously stirred during the whole process. When the desired temperature was reached, n-butyllithium (0.045 mmol) was added, to perform quenching of residual impurities. Then, n-butyllithium (0.845 mmol) was added to initiate the polymerization process. The reaction was carried out as a isothermic process for 60 minutes. After this time, silicon tetrachloride ($5.25 \times 10^{-2}$ mmol) was added to the polymer solution as a coupling agent. Coupling was performed for 5 minutes. The reaction solution was terminated, using nitrogen-purged isopropyl alcohol (1 mmol), and rapidly stabilized by addition of 2-methyl-4,6-bis(octylsulfanylmethyl)phenol (at 1.0 phr polymer). The polymer solution was treated with isopropanol, and precipitation of polymer occurred. The final product was dried overnight in a vacuum oven.

Example 2b (Myrcene Derivative from Example 1a as Comonomer)

Cyclohexane (820 g) was added to the inerted two-liter reactor, followed by addition of styrene (31 g), functionalized myrcene of Example 1a (0.75 g) and 1,3-butadiene (117 g). Inhibitor from styrene and 1,3-butadiene was removed. Next, 2,2-bis(2-tetrahydrofuryl)propane (DTHFP, 2.52 mmol) was added, to provide random incorporation of styrene monomer and to increase the vinyl content, from the butadiene-derived units. The solution inside the reactor was heated to 60° C. and continuously stirred during the whole process. When the desired temperature was reached, n-butyllithium (0.045 mmol) was added, to perform quenching of residual impurities. Then, n-butyllithium (0.845 mmol) was added to initiate the polymerization process. The reaction was carried out as a isothermic process for 60 minutes. After this time, silicon tetrachloride ($6.30 \times 10^{-2}$ mmol) was added to the polymer solution as a coupling agent. Coupling was performed for 5 minutes. The reaction solution was terminated, using nitrogen-purged isopropyl alcohol (1 mmol), and rapidly stabilized by addition of 2-methyl-4,6-bis(octylsulfanylmethyl)phenol (at 1.0 phr polymer). The polymer solution was treated with isopropanol, and precipitation of polymer occurred. The final product was dried overnight in a vacuum oven.

Example 3b (Myrcene Derivative from Example 1a as Both Initiator Component and as Comonomer)

Cyclohexane (820 g) was added to the inerted two-liter reactor, followed by addition of styrene (31 g), functionalized myrcene of Example 1a (0.50 g) and 1,3-butadiene (117 g). Inhibitor from styrene and 1,3-butadiene was removed. Next, 2,2-bis(2-tetrahydrofuryl)propane (DTHFP, 3.69 mmol) was added as a styrene randomizer and to increase the vinyl content, from the butadiene-derived units. The solution inside the reactor was heated to 60° C. and continuously stirred during the whole process. When the temperature was reached, n-butyllithium (0.045 mmol) was added to the reactor, to perform quenching of residual impurities.

n-Butyllithium (1.23 mmol) and functionalized myrcene of Example 1a (0.25 g) were mixed together in a burette, the contact time was about 15 min, and then the mixture was added to initiate the polymerization process. The reaction was carried out over 60 minutes, as an isothermic process. After this time, silicon tetrachloride ($6.30 \times 10^{-2}$ mmol) was added to the polymer solution as a coupling agent. Coupling was performed for 5 minutes. The reaction solution was terminated, using nitrogen-purged isopropyl alcohol (1 mmol), and rapidly stabilized by addition of 2-methyl-4,6-bis(octylsulfanylmethyl)phenol (at 1.0 phr polymer). The polymer solution was treated with isopropanol, and precipitation of polymer occurred. The final product was dried overnight in a vacuum oven.

Example 4b (Continuous Polymerization)

A butadiene-styrene copolymer was prepared in a cascade of three continuous reactors having a volume of 10 L (reactor 1), 20 L (reactor 2) and 10 L (reactor 3), respectively, where each reactor was equipped with a paddle stirrer. The agitation speed was 150-200 rpm and filling factor at the level of 50%-60%. Hexane, styrene, 1,3-butadiene, 1,2-butadiene (gel formation prevention additive), DTHFP and functionalized myrcene of Example 1a (the last three reactants as solutions in hexane) were dosed into the first reactor, with flow rates of 10752.00 g/h, 398.00 g/h, 1499.00 g/h, 19.00 g/h, 102.00 g/h and 46.03 g/h, respectively. n-Butyllithium flow rate (as a solution in hexane) was 107.00 g/h, and functionalized myrcene of Example 1a (as a solution in hexane) flow rate was 141.48 g/h. Streams of n-butyllithium and 50/50 by weight of functionalized myrcene of Example 1a were mixed together in the pipe static mixer, before entering the reactor, and the contact time was about 15 min. The temperature in the reactors was between 70° C. to 85° C. To obtain branched rubber silicon tetrachloride was added at the reactor 3 inlet, at the entry of static mixer, in a $SiCl_4$/active n-butyllithium ratio of 0.05. The coupling reaction was performed at 70-85° C. At the reactor 3 outlet, 2-methyl-4,6-bis(octylsulfanylmethyl)phenol (as a solution in hexane) was added as an antioxidant (142 g/h).

The polymer solution was subsequently transferred to a stripper. Distilled water, in an amount of double of the total mass of polymer solution, as well as pH regulator and soap were added to the polymer solution, and the stripper contents were then treated with steam. Steam-stripping was carried out until the entire amount of solvent had been removed, and rubber crumbs were obtained. Then, the rubber crumbs were removed from the stripper, cooled to room temperature, milled and dried in a stream of hot air.

Characterization

Vinyl Content (%)

Determined by 600 MHz $^1$H-NMR, based on BS ISO 21561:2005.

Bound Styrene Content (%)

Determined by 600 MHz $^1$H-NMR, based on BS ISO 21561:2005.

Molecular Weight Determination

Gel permeation chromatography was performed via PSS Polymer Standards Service multiple columns (with guard column) using THF as the eluent and for sample preparation. Multi-angle laser light scattering measurements were carried out using a Wyatt Technologies Dawn Heleos II light scattering detector, DAD (PDA) Agilent 1260 Infinity UV-VIS detector and Agilent 1260 Infinity refractive index detector.

Glass Transition Temperature (° C.)

Determined based on PN-EN ISO 11357-1:2009.

Mooney Viscosity (ML (1+4)/100° C.)

Determined based on ASTM D 1646-07, using a large rotor under the conditions of preheating=1 minute, rotor operating time=4 minutes, and temperature=100° C.

Vulcanization Characteristics

Determined based on ASTM D6204, using RPA 2000 Alpha Technologies rubber processing analyzer, operating time=30 minutes, and temperature=170° C.

Evaluation and Measurement of Properties of Rubber Composition

A vulcanized rubber compound was prepared using a polymer obtained in each of Examples, and was measured for the following test parameters.

i) Tire Predictors (Tan δ at 60° C., Tan δ at 0° C., Tan δ at −10° C.)

A vulcanized rubber compound was used as a test sample and measured for this parameter, using a dynamic mechanical analyzer (DMA 450+ MetraviB) in single shear mode under the conditions of dynamic strain=2%, frequency=10 Hz, in the temperature range of from −70 to 70° C., with a heating rate of 2.5 K/min.

ii) Rebound Resilience

Determined based on ISO 4662.

Table 1 shows the characterization results for the four samples synthesized for this study.

TABLE 1

| Example | $M_n$ [g/mol] | $M_w$ [g/mol] | $M_w/M_n$ | Vinyl content [%][1] | Styrene content [%] | % F [% wt.] | MV [1 + 4] | Tg [° C.] |
|---|---|---|---|---|---|---|---|---|
| 1b (comp.) | 223,300 | 319,500 | 1.43 | 62.4 | 21.2 | 0.00 | 58.7 | −25.1 |
| 2b | 227,500 | 316,800 | 1.39 | 61.8 | 20.9 | 0.49 | 61.5 | −24.2 |
| 3b | 224,800 | 322,800 | 1.44 | 62.0 | 21.3 | 0.47 | 60.2 | −25.0 |
| 4b | 186,400 | 328,600 | 1.76 | 62.1 | 21.5 | 0.47 | 53.8 | −23.9 |

[1]Based on 1,3-butadiene content

Compounding

Using the rubbers obtained in Examples 2b, 3b, 4b and Comparative Example 1b, respectively, compounding was made according to the "compounding recipe of rubber composition" shown in Table 2. The compounding of the solution styrene-butadiene rubber, fillers, and rubber additives was performed in a Banbury type of internal mixer (350E Brabender GmbH& Co. KG) and on a lab-sized two roll mill. The rubber compounds were mixed in two different stages and the final pass was completed on a two roll mill. The first stage was used to mix the polymer with oil, silica, silane coupling agent, 6PPD and activators in several steps. The second stage was to further improve the distribution of the silica along with adding of carbon black, then the compound was allowed to sit for 24 hours. In order to be conditioned for the final pass, the rubber compound was allowed to condition for four hours. The final mixing was performed on a two roll mill. The last step was used to add the cure packages. Then, each compound was vulcanized at 170° C., for $T_{95+1.5}$ minutes (based on RPA results), to obtain vulcanizates. Each vulcanized rubber compound was evaluated and measured for the above-mentioned curing characteristics, tire predictors and rebound resilience. The results are shown in Table 3.

TABLE 2

| Component | phr |
|---|---|
| SBR | 75 |
| Polybutadiene rubber[1] | 25 |
| Silica[2] | 80 |

TABLE 2-continued

| Component | phr |
|---|---|
| Carbon Black[3] | 10 |
| Stearic acid | 2 |
| Zinc oxide | 3 |
| Oil extender[4] | 37.5 |
| 6PPD[5] | 2 |
| Bis[3-(triethoxysilyl)propyl]tetrasulfide[6] | 6.4 |
| N-tert-butyl-2-benzothiazole sulfenamide[7] | 1.7 |
| 1,3-Diphenylguanidine[8] | 2 |
| Sulphur | 1.5 |

[1]Synteca 44, a product of Synthos
[2]Zeosil 1165MP, a product of Solvay
[3]ISAF-N234, a product of Cabot Corporation
[4]VivaTec 500, a product of Klaus Dahleke KG
[5]VULKANOX 4020/LG, a product of Lanxess
[6]Si 69, a product of Evonik
[7]LUVOMAXX TBBS, a product of Lehmann & Voss & Co. KG
[8]DENAX, a product of Draslovka a.s.

TABLE 3

| Example | Rebound re-silience (23° C.), [%] | Rebound re-silience (70° C.), [%] | tan δ (60° C.) | tan δ, (0° C.) | tan δ, (−10° C.) |
|---|---|---|---|---|---|
| 1c (comp.) | 32.1 | 54.9 | 0.189 | 0.513 | 0.664 |
| 2c | 34.9 | 60.8 | 0.149 | 0.648 | 0.757 |
| 3c | 37.9 | 65.9 | 0.135 | 0.646 | 0.791 |
| 4c | 38.7 | 67.2 | 0.143 | 0.682 | 0.945 |

It is apparent from these results that in a silica mix, as judged based on the properties in the vulcanized state, SSBR 3b according to the invention imparts to the corresponding rubber composition 3c reinforcement properties which are superior to those obtained with the control SSBR 1b and with the other SSBR 2b according to the invention. Moreover, the data in Table 3 shows that SSBR 4b obtained in continuous polymerization has better reinforcement properties compared to control SSBR 1b and SSBR 2b.

Furthermore, the tire predictors of rubber composition 3c according to the invention are improved relative to those of the control rubber composition 1c and of the rubber compositions 2c and 4c (in terms of rolling resistance) according to the invention. Moreover, said tire predictors are improved for rubber composition 2c according to the invention relative to the control rubber composition 1c. Furthermore, tire predictors are improved for rubber composition 4c according to the invention relative to the control rubber composition 1c; additionally, ice traction and dry traction properties are improved relative to those of rubber compositions 1c, 2c, and 3c.

II.2 Application of Functionalized Myrcene in Coordination Polymerization

In order to provide more details about the synthesis and properties of elastomers produced according to the present invention, functionalized butadiene homopolymer with functional groups are described in Examples 6b and 8b below, and are compared with a non-functionalized homopolymer as described in Comparative Examples 5b and 7b. The amounts of starting materials used in these examples are listed in Table 4. The measurement methods and evaluation methods of properties are shown below.

Polymerization (for Additional Information, See Also the Above Information Relating to Anionically Obtained Polymers)

For catalyst composition and procedure, see the following publications:
1. Lars Friebe, Oskar Nuyken and Werner Obrecht, "A Comparison of Neodymium Versatate, Neodymium Neopentanolate and Neodymium Bis(2-ethylhexyl) phosphate in Ternary Ziegler Type Catalyst Systems With Regard to their Impact on the Polymerization of 1,3-Butadiene", in J. Macromol. Sci. A., (2005), 42, 7, 839-851.
2. Friebe, L., Nuyken, O., Windisch, H., and Obrecht, W. "Polymerization of 1,3-butadiene initiated by neodymium versatate/diisobutylaluminum hydride/ethylaluminum sesquichloride: Kinetics and conclusions about the reaction mechanism", in Macromol. Chem. Phys., (2002), 203, 8, 1055-1064.

General Polymerization Description:

A twenty litre reactor was filled with dry 1,3-butadiene and dry solvent (cyclohexane), and functionalized myrcene of Example 1a, and heated to 60° C. Then, catalyst was added in the following sequence: neodymium bis(2-ethylhexyl)phosphate (NdP), diisobutylaluminum hydride (DIBAH) (both 0.1 mol/L solutions in cyclohexane). Polymerization was started by addition of ethylaluminum sesquichloride (EASC) (1.0 mol/L solution in cyclohexane). The solution inside the reactor was heated and continuously stirred during the whole process. The temperature of the reaction mixture was kept between 60 and 90° C. The reaction solution was terminated, using nitrogen-purged isopropyl alcohol, and was rapidly stabilized by the addition of 2-methyl-4,6-bis(octylsulfanylmethyl)phenol (at 1.0 phr polymer).

The polymers were recovered by a conventional recovery operation using steam stripping of the solvent and were dried in a stream of hot air.

Details of the reaction conditions, of the used recipes and characteristics of the obtained polymers are included in Table 4 below.

Characterization (Additional Information, See Also the Above Information Relating to Anionically Obtained Polymers)

Vinyl Content, Cis-1,4 Content, Trans-1,4 Content (%)

The microstructure of butadiene rubber was determined by infrared spectroscopy (Thermo Scientific Nicolet Is10).

The following peaks were used for quantitative determination of the poly(butadiene) microstructure:
735 cm$^{-1}$ ($\delta$(cis-R—CH=CR—H), →cis-1,4, $\epsilon$=0.192),
912 cm$^{-1}$ ($\delta$(R—CH=CH—H), →vinyl (1,2), $\epsilon$=1.0),
965 cm$^{-1}$ ($\delta$(trans-R—CH=CR—H), →trans-1,4, $\epsilon$=0.769).

The methodology is described in:
1. M. Kraft, Struktur und Absorptionsspektroskopie der Kunststoffe, VCH, Weinheim 1973, p. 93; and
2. E. O. Schmalz, W. Kimmer, Z. Anal. Chem. 1961, 181, 229.

Evaluation and Measurement of Properties of Vulcanized Rubber Composition (Additional Information, See Also the Above Information Relating to Anionically Obtained Polymers)

A vulcanized rubber compound was produced using a polymer obtained in each of the examples, and was measured for the following test parameters i) Tire Predictors (Tan $\delta$ at 60° C., Tan $\delta$ at 0° C., Tan $\delta$ at −10° C., J" at 30° C.)

A vulcanized rubber composition was used as a test sample and measured for this parameter, using a dynamic mechanical analyzer (DMA 450+ MetraviB) in shear mode under the conditions of tensile strain=2%, frequency=10 Hz, in a temperature range of from −80 to 80° C., with a heating rate of 2.5 K/min.

ii) Rebound Resilience
   Determined based on ISO 4662 iii) Reinforcement Factor
   Expressed as ratio between Modulus 300% and Modulus 100%, Determined based PN-ISO 37:2007 using Zwick/Roel Z005 iv) Silica Dispersion
   Determined based ISO 1134 C, D, E; ASTM D7723, using disperGRADER Alpha Technologies Compounding (Additional Information, See Also the Above Information Relating to Anionically Obtained Polymers)

Using the rubbers as obtained in Examples 6b and 8b and Comparative Examples 5b and 7b, respectively, compounding was made according to the compounding recipe as shown in Table 5. The compounding of the solution styrene-butadiene rubber, fillers, and rubber additives was performed in a Farrel type of internal mixer (Mixer Farrel BR+1600) and on a lab sized two roll mill. The rubber compounds were mixed in three different stages, first two on internal mixer, and third one (final pass) was completed on a two roll mill.

The first stage was used to mix the rubbers with oil, silica, silane coupling agent, 6PPD and activators in several steps.

TABLE 4

Reactions conditions and obtained polymers characteristics (coordination polymerization), where $n_M/n_{Nd}$ - represents the molar ratio of monomer to neodymium, $n_{Cl}/n_{Nd}$ - represents the molar ratio of chloride to neodymium, $n_{DIBAH}/n_{Nd}$ - represents the molar ratio of DIBAH to neodymium, F % - represents content by weight percent of functionalized myrcene in the polymer chains.

| | Reaction conditions | | | | | | GPC results | | | FTIR results [%] | | | DSC | | |
|---|---|---|---|---|---|---|---|---|---|---|---|---|---|---|---|
| Ex. | $T_{init}$ [° C.] | Cyclohexane [g] | 1,3-butadiene [g] | $n_M/n_{Nd}$ | $n_{Cl}/n_{Nd}$ | $n_{DIBAH}/n_{Nd}$ | Mn [kg/mol] | Mw [kg/mol] | Mw/Mn | Vinyl | 1,4-cis | 1,4-trans | results Tg, ° C. | % F [% wt.][1] | MV [1 + 4] |
| 5b | 60 | 12000 | 1500 | 9250 | 2 | 6 | 150.2 | 282.3 | 1.88 | 0.3 | 98.2 | 1.9 | −105.2 | 0 | 62.1 |
| 6b | 60 | 12000 | 1500 | 9250 | 2 | 7 | 141.7 | 258.1 | 1.79 | 0.3 | 98.0 | 1.8 | −104.9 | 0.50 | 60.2 |
| 7b | 60 | 12000 | 1500 | 9250 | 2 | 8 | 120.5 | 245.6 | 2.04 | 0.2 | 97.9 | 2.0 | −104.7 | 0 | 43.6 |
| 8b | 60 | 12000 | 1500 | 9250 | 2 | 8 | 123.7 | 249.2 | 2.01 | 0.3 | 98.1 | 1.9 | −105.1 | 0.50 | 47.1 |

[1]Theoretical value, some signals from catalyst overlap signals from functionalized diene The second stage was performed to further improve the distribution of the silica along with adding of carbon black, then the compound was conditioned for 24 hours. The final mixing was performed on a two roll mill. The last step was used to add the cure packages. Then, each compound was vulcanized at 170° C., for $T_{95+1.5}$ minutes (based on RPA results), to obtain vulcanizates. Each vulcanized rubber compound was evaluated and measured for the above-mentioned curing characteristics, Payne effect and tire predictors. The results are shown in Table 6.

TABLE 5

| Component | phr | Mixing stage |
|---|---|---|
| SBR[1] | 52 | 1 |
| Polybutadiene rubber | 48 | 1 |
| Silica[2] | 80 | 1 |
| Carbon Black[3] | 5 | 2 |
| Stearic acid | 2 | 1 |
| Zinc oxide | 2 | 1 |
| Oil extender[4] | 28 | 1 |
| 6PPD[5] | 2 | 1 |
| Antioxidant[6] | 2 | 1 |
| Wax[7] | 2 | 1 |
| Bis[3-(triethoxysilyl)propyl]tetrasulfide[8] | 6.4 | 1 |
| N-tert-butyl-2-benzothiazole sulfenamide[9] | 1.6 | 3 |
| 1,3-Diphenylguanidine[10] | 2 | 3 |
| Sulphur | 1.5 | 3 |

[1]Syntion 2150, a product of Synthos R&D, specification: non functionalized rubber, Mn~202 kg/mol, Mw ~395 kg/mol, Mw/Mn = 1.95, styrene content 21.5%, vinyl 50.6% (/polymer), Tg~−25° C.,
[2]Zeosil 1165MP, a product of Solvay,
[3]ISAF-N234, a product of Cabot Corporation,
[4]VivaTec 500, a product of Klaus Dahleke KG,
[5]VULKANOX 4020/LG, a product of Lanxess,
[6]TMQ luvomaxx,
[7]MC Wax 721,
[8]Si 69, a product of Evonik,
[9]LUVOMAXX TBBS, a product of Lehmann & Voss & Co. KG,
[10]DENAX, a product of Draslovka a.s.

TABLE 6

| Ex. | % F [% wt.] | MV [1 + 4] (60° C.)[1] | tan δ (60° C.)[1] | J" (30° C.)[2] [Pa$^{-1}$] | G' [Pa]/ E' (−20° C.)[3] [MPa] | Rebound[4] at $T_{70° C.}$ | RI (S300%/S100%)[5] | Silica Dispersion[6] [%] |
|---|---|---|---|---|---|---|---|---|
| 5c | 0 | 62.1 | 0.189 | 4.60E−08 | 1.65E+07 | 58 | 4.2 | 81 |
| 6c | 0.50 | 60.2 | 0.159 | 5.08E−08 | 1.21E+07 | 62 | 4.8 | 92 |
| 7c | 0 | 43.6 | 0.192 | 5.05E−08 | 1.63E+07 | 59 | 4.3 | 80 |
| 8c | 0.50 | 47.1 | 0.161 | 4.79E−08 | 1.25E+07 | 63 | 4.7 | 93 |

[1]Rolling resistance (lower is better)
[2]Dry traction (higher is better)
[3]Winter Traction (lower is better)
[4]Rebound at 70° C. (higher is better)
[5]Reinforcement index (higher is better)
[6]Silica dispersion (higher is better)

The rubbers as obtained in Examples 6c and 8c and Comparative Examples 5c and 7c, respectively, were examined and compared to each other (functionalized vs. nonfunctionalized), see the results presented in Table 6.

Example 5c was compared with Example 6c, and Example 7c with Example 8c, since they correspond to similar Mooney ranges, namely higher (58, 64) and lower (44, 51).

In each case, tire predictors obtained from DMA, such as rolling resistance, dry traction, winter traction are improved when comparing functionalized (Ex. 6c, 8c—Table 6) and nonfunctionalized (Ex. 5c, 7c—Table 6) rubber, the same is true with respect to rebound at high temperature. The reinforcement index, the ratio of modulus 300% to modulus 100%, was also found to be increased, as well as much higher silica dispersion (dispeGRADER). This confirmed a much higher interaction between functionalized cis-polybutadiene rubber and filler (silica), as compared to the use of non-functionalized rubber.

While certain representative embodiments and details have been shown for the purpose of illustrating the subject invention, it will be apparent to those skilled in this art that various changes and modifications can be made therein without departing from the scope of the subject invention, which scope is defined by the following claims.

The invention claimed is:

1. A method for the preparation of a functionalized conjugated diene selected from the group of compounds of formula (Ia), (Ib), (Ic)

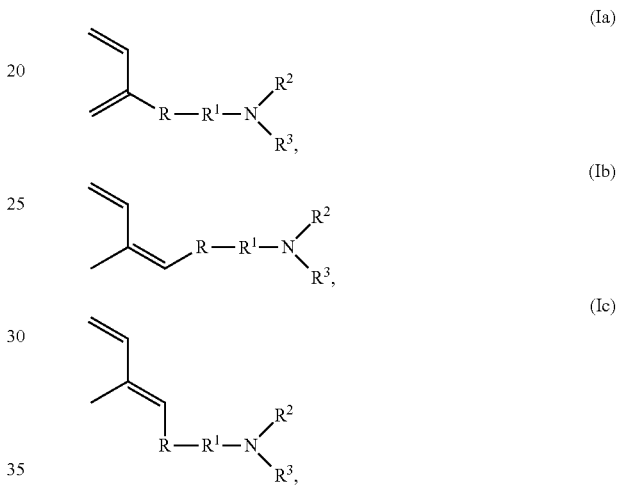

wherein
R is a branched, unsaturated hydrocarbylene group, and wherein R in Formula (Ia) has at least 6 carbon atoms and R in Formula (Ib) or (Ic) has at least 5 carbon atoms,
$R^1$ is selected from
  i) a single bond,
  ii) one or more of an oxygen atom, a sulfur atom, and a group $NR^4$; and
  iii) an organylene group optionally containing one or more selected from an oxygen atom, a sulfur atom, and a group $NR^4$;
$R^2$ and $R^3$ can be the same or different and represent $Si(R^5)_3$, wherein each $R^5$ can be the same or different and represents an organyl group optionally containing one or more heteroatoms selected from an oxygen atom, a sulfur atom, a nitrogen atom, and a silicon atom;

$R^4$ represents an organyl group optionally containing one or more heteroatoms selected from an oxygen atom, a sulfur atom, a nitrogen atom, and a silicon atom;

the method comprising reacting a conjugated diene halide selected from the group of compounds of formula (IIIa), (IIIb), (IIIc)

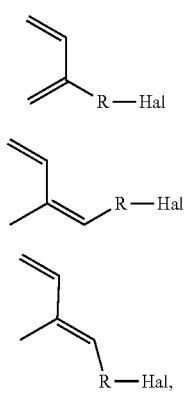

(IIIa)

(IIIb)

(IIIc)

wherein Hal is selected from fluorine, chlorine, bromine, and iodine atoms, with an amide of formula (IV)

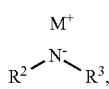

(IV)

wherein M is an alkali metal selected from lithium, sodium, and potassium.

2. A functionalized conjugated diene selected from the group of compounds of formula (Ia), (Ib), (Ic)

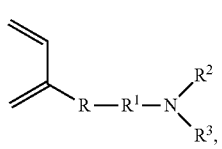

(Ia)

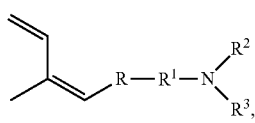

(Ib)

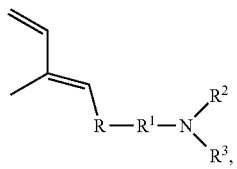

(Ic)

wherein

R is a branched, unsaturated hydrocarbylene group, and R is characterized in that a R-containing conjugated diene selected from the group of compounds of formula (IIa), (IIb), (IIc)

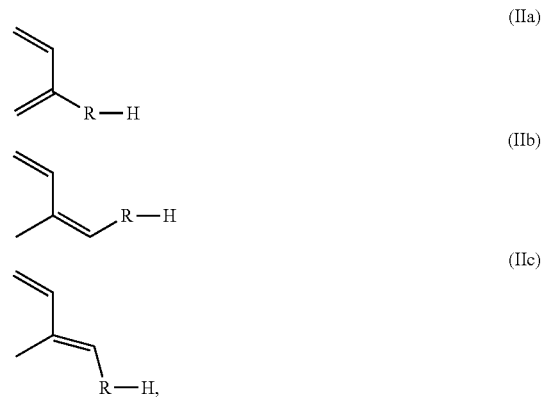

(IIa)

(IIb)

(IIc)

is a conjugated diene selected from terpenes and 4,8-dimethyl-1,3,7-nonatriene, $R^1$ is selected from
  i) a single bond,
  ii) one or more of an oxygen atom, a sulfur atom, and a group $NR^4$; and
  iii) an organylene group optionally containing one or more selected from an oxygen atom, a sulfur atom, and a group $NR^4$;

$R^2$ and $R^3$ can be the same or different and represent $Si(R^5)_3$, wherein each $R^5$ can be the same or different and represents an organyl group optionally containing one or more heteroatoms selected from an oxygen atom, a sulfur atom, a nitrogen atom, and a silicon atom;

$R^4$ represents an organyl group optionally containing one or more heteroatoms selected from an oxygen atom, a sulfur atom, a nitrogen atom, and a silicon atom.

3. The functionalized conjugated diene of claim 2, which is a myrcene derivative of formula (Ia1), (Ib1), or (Ic1)

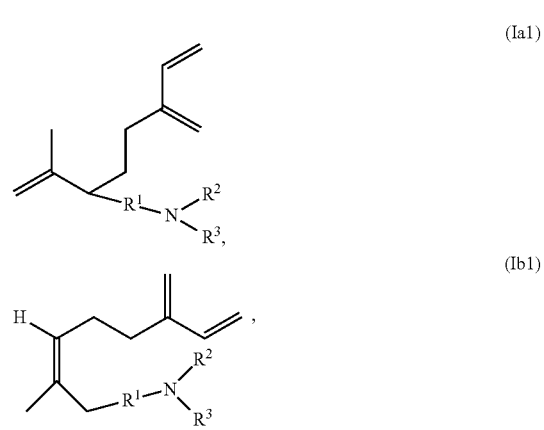

(Ia1)

(Ib1)

-continued

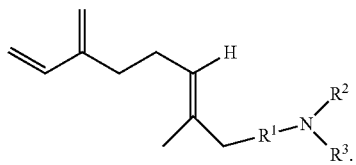
(Ic1)

4. The functionalized conjugated diene of any of claim 2, wherein $R^2$ and $R^3$ are the same.

5. The functionalized conjugated diene of claim 4, wherein each $R^5$ is the same and represents a linear or branched, saturated or unsaturated hydrocarbyl group.

6. The functionalized conjugated diene of claim 5, which is a myrcene derivative of formula (Ia2), (Ib2), or (Ic2)

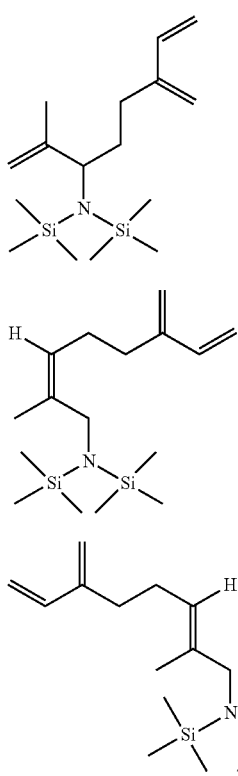

(Ia2)

(Ib2)

(Ic2)

7. A method of producing an elastomeric copolymer, the method comprising copolymerizing one or more functionalized conjugated dienes of claim 2 with one or more conjugated diene monomers.

8. The use of claim 7, wherein the conjugated diene monomer is selected from 1,3-butadiene, isoprene, 1,3-pentadiene, 2,3-dimethyl-1,3-butadiene, 2-methyl-1,3-pentadiene, 2,3-dimethyl-1,3-pentadiene, 2-phenyl-1,3-butadiene, and 4,5-diethyl-1,3-octadiene.

9. The use of claim 7, wherein the copolymerizing is by anionic polymerization or by coordination polymerization.

10. The use of any of claim 7, wherein the copolymerizing further comprises copolymerization of one or more vinyl aromatic monomers.

11. The method of claim 7, wherein the amount of the one or more functionalized conjugated dienes is in a range of from 0.05 to 5 wt. %, based on the weight of the elastomeric copolymer.

12. A method of producing an elastomeric copolymer, the methd comprising copolymerizing one or more conjugated diene monomers, optionally one or more vinyl aromatic monomers, and optionally one or more functionalized conjugated dienes selected from of the group of compounds of formula (Ia), (Ib), (Ic), by anionic copolymerization in the presence of an alkali metal salt derivative of a functionalized conjugated diene selected from the group of compounds of formula (Ia), (Ib), (Ic) as initiator for the anionic copolymerization, wherein formulae (Ia), (Ib), (Ic) are as follows:

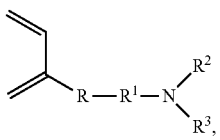
(Ia)

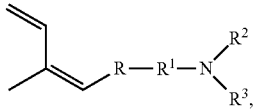
(Ib)

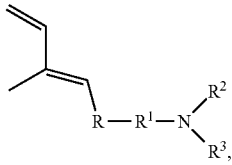
(Ic)

wherein
R is a branched, unsaturated hydrocarbylene group, and R is characterized in that a R-containing conjugated diene selected from the group of compounds of formula (IIa), (IIb), (IIc)

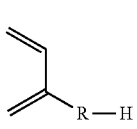
(IIa)

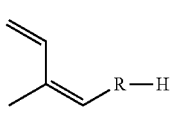
(IIb)

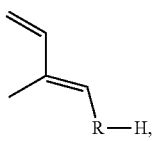
(IIc)

is a conjugated diene selected from terpenes and 4,8-dimethyl-1,3,7-nonatriene,
$R^1$ is selected from
  i) a single bond,
  ii) one or more of an oxygen atom, a sulfur atom, and a group $NR^4$; and
  iii) an organylene group optionally containing one or more selected from an oxygen atom, a sulfur atom, and a group $NR^4$;
$R^2$ and $R^3$ can be the same or different and represent $Si(R^5)_3$, wherein each $R^5$ can be the same or different and represents an organyl group optionally containing one or more heteroatoms selected from an oxygen atom, a sulfur atom, a nitrogen atom, and a silicon atom;

$R^4$ represents an organyl group optionally containing one or more heteroatoms selected from an oxygen atom, a sulfur atom, a nitrogen atom, and a silicon atom.

13. A process for the production of a copolymer component comprising coupled copolymer and terminally modified copolymer, the process comprising the following steps:

(1) providing an initiator component, wherein the initiator component optionally comprises one or more alkali metal salt derivatives of a one or more functionalized conjugated dienes selected from the group of compounds of formula (Ia), (Ib), (Ic)

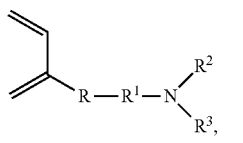
(Ia)

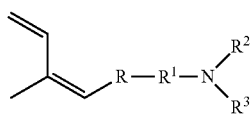
(Ib)

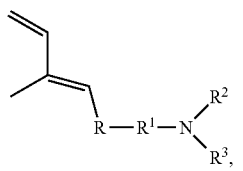
(Ic)

wherein
R is a branched, unsaturated hydrocarbylene group, and R is characterized in that a R-containing conjugated diene selected from the group of compounds of formula (IIa), (IIb), (IIc)

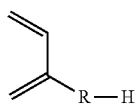
(IIa)

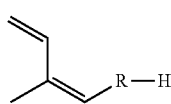
(IIb)

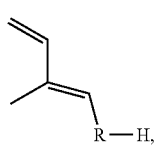
(IIc)

is a conjugated diene selected from terpenes and 4,8-dimethyl-1,3,7-nonatriene, $R^1$ is selected from
i) a single bond,
ii) one or more of an oxygen atom, a sulfur atom, and a group $NR^4$; and
iii) an organylene group optionally containing one or more selected from an oxygen atom, a sulfur atom, and a group $NR^4$;

$R^2$ and $R^3$ can be the same or different and represent $Si(R^5)_3$, wherein each $R^5$ can be the same or different and represents an organyl group optionally containing one or more heteroatoms selected from an oxygen atom, a sulfur atom, a nitrogen atom, and a silicon atom;

$R^4$ represents an organyl group optionally containing one or more heteroatoms selected from an oxygen atom, a sulfur atom, a nitrogen atom, and a silicon atom, wherein the alkali metal is selected from lithium, sodium, and potassium;

(2) contacting a monomer component comprising
i) optionally one or more functionalized conjugated dienes selected from the group of compounds of formula (Ia), (Ib), (Ic),
ii) one or more conjugated diene monomers and
iii) optionally one or more vinyl aromatic monomers,
with the initiator component, to initiate anionic copolymerization;

(3) continuing copolymerization, to result in a copolymer;
(4) optionally continuing copolymerization of the copolymer, in the presence of one or more functionalized monomers, to result in a functionalized copolymer;
(5) coupling a part of the copolymer of step (3) or the functionalized copolymer of step (4) with one or more coupling agents, to result in coupled copolymer;
(6) terminally modifying a part of the copolymer of step (3) or the functionalized copolymer of step (4) with one or more terminal modifying agents, to result in terminally modified copolymer;
(7) optionally post-polymerization modification of the copolymer of step (3), or the functionalized copolymer of step (4), or the coupled copolymer of step (5), or the terminally modified copolymer of step (6), by
a. re-initiating with an initiator component to initiate anionic copolymerization, and
b. continuing copolymerization, in the presence of one or more functionalized monomers, to result in copolymer with functionalized side-groups;

wherein the functionalized conjugated diene selected from the group of compounds of formula (Ia), (Ib), (Ic) is used in at least one of steps (1) and (2).

14. A process for producing an elastomeric copolymer comprising subjecting i) one or more functionalized conjugated dienes selected from the group of compounds of formula (Ia), (Ib), (Ic)

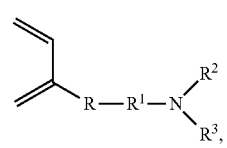
(Ia)

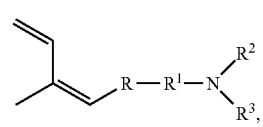
(Ib)

-continued

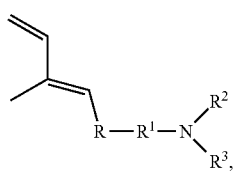
(Ic)

wherein
R is a branched, unsaturated hydrocarbylene, and R is characterized in that a R-containing conjugated diene selected from the group of compounds of formula (IIa), (IIb), (IIc)

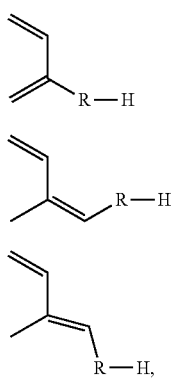

(IIa)

(IIb)

(IIc)

is a conjugated diene selected from terpenes and 4,8-dimethyl-1,3,7-nonatriene, $R^1$ is selected from
  i) a single bond,
  ii) one or more of an oxygen atom, a sulfur atom, and a group $NR^4$; and
  iii) an organylene group optionally containing one or more selected from an oxygen atom, a sulfur atom, and a group $NR^4$;

$R^2$ and $R^3$ can be the same or different and represent $Si(R^5)_3$, wherein each $R^5$ can be the same or different and represents an organyl group optionally containing one or more heteroatoms selected from an oxygen atom, a sulfur atom, a nitrogen atom, and a silicon atom;

$R^4$ represents an organyl group optionally containing one or more heteroatoms selected from an oxygen atom, a sulfur atom, a nitrogen atom, and a silicon atom, ii) one or more conjugated diene monomers, and
iii) optionally one or more vinyl aromatic monomers
  to anionic polymerization conditions,
  wherein the anionic polymerization conditions include initiating the polymerization with an alkali metal salt derivative of the one or more functionalized conjugated dienes of formula (Ia), (Ib), (Ic), wherein the alkali metal is selected from lithium, sodium, and potassium.

15. A process for producing an elastomeric copolymer comprising subjecting
  i) one or more functionalized conjugated dienes selected from the group of compounds of formula (Ia), (Ib), (Ic)

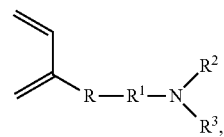
(Ia)

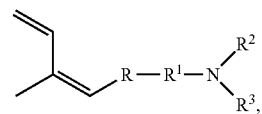
(Ib)

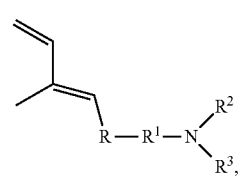
(Ic)

wherein
R is a branched, unsaturated hydrocarbylene group, and R is characterized in that a R-containing conjugated diene selected from the group of compounds of formula (IIa), (IIb), (IIc)

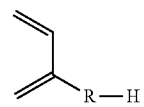
(IIa)

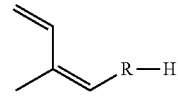
(IIb)

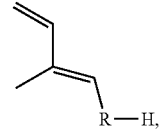
(IIc)

is a conjugated diene selected from terpenes and 4,8-dimethyl-1,3,7-nonatriene, $R^1$ is selected from
  i) a single bond,
  ii) one or more of an oxygen atom, a sulfur atom, and a group $NR^4$; and
  iii) an organylene group optionally containing one or more selected from an oxygen atom, a sulfur atom, and a group $NR^4$;

$R^2$ and $R^3$ can be the same or different and represent $Si(R^5)_3$, wherein each $R^5$ can be the same or different and represents an organyl group optionally containing one or more heteroatoms selected from an oxygen atom, a sulfur atom, a nitrogen atom, and a silicon atom;

$R^4$ represents an organyl group optionally containing one or more heteroatoms selected from an oxygen atom, a sulfur atom, a nitrogen atom, and a silicon atom, and
  ii) one or more conjugated diene monomers
to Ziegler-Natta polymerization conditions.

16. The process of claim 15, wherein the Ziegler-Natta polymerization conditions include a catalyst system comprising 1) metal chloride and 2) co-catalyst.

17. The process of claim 15, wherein the Ziegler-Natta polymerization conditions include a catalyst system comprising 1) non-halide metal compound, 2) co-catalyst, and 3) halide donor compound.

18. An elastomeric copolymer comprising repeat units that are derived from
A) 0.05 wt. % to 5 wt. %, by weight of the copolymer, of one or more functionalized conjugated dienes selected from the group of compounds of formula (Ia), (Ib), (Ic)

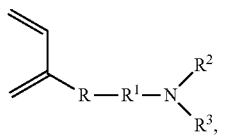
(Ia)

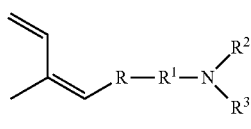
(Ib)

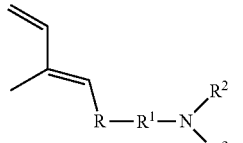
(Ic)

wherein
R is a branched, unsaturated hydrocarbylene group, and R is characterized in that a R-containing conjugated diene selected from the group of compounds of formula (IIa), (IIb), (IIc)

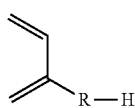
(IIa)

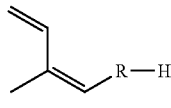
(IIb)

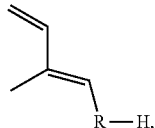
(IIc)

is a conjugated diene selected from terpenes and 4,8-dimethyl-1,3,7-nonatriene,
$R^1$ is selected from
  i) a single bond,
  ii) one or more of an oxygen atom, a sulfur atom, and a group $NR^4$; and
  iii) an organylene group optionally containing one or more selected from an oxygen atom, a sulfur atom, and a group $NR^4$;
$R^2$ and $R^3$ can be the same or different and represent $Si(R^5)_3$, wherein each $R^5$ can be the same or different and represents an organyl group optionally containing one or more heteroatoms selected from an oxygen atom, a sulfur atom, a nitrogen atom, and a silicon atom;
$R^4$ represents an organyl group optionally containing one or more heteroatoms selected from an oxygen atom, a sulfur atom, a nitrogen atom, and a silicon atom,
B) 45 wt. % to 99.95 wt. %, by weight of the copolymer, of one or more conjugated diene monomers;
C) 0 wt. % to 50 wt. %, by weight of the copolymer, of one or more vinyl aromatic monomers.

19. The elastomeric copolymer of claim 18, wherein the amount of B) conjugated diene monomer is 50 to 92 wt. %, by weight of the copolymer.

20. The elastomeric copolymer of claim 18, wherein the vinyl aromatic monomer is selected from styrene, 1-vinylnaphthalene, 3-methylstyrene, 3,5-diethylstyrene, 4-propylstyrene, 2,4,6-trimethylstyrene, 4-dodecylstyrene, 3-methyl-5-n-hexylstyrene, 4-phenylstyrene, 2-ethyl-4-benzylstyrene, 3,5-diphenylstyrene, 2,3,4,5-tetraethylstyrene, 3-ethyl-1-vinylnaphthalene, 6-isopropyl-1-vinylnaphthalene, 6-cyclohexyl-1-vinylnaphthalene, 7-dodecyl-2-vinylnaphthalene, and α-methylstyrene.

21. The elastomeric copolymer of claim 18 wherein the amount of C) vinyl aromatic monomer is 8 to 45 wt. %, by weight of the copolymer.

22. The elastomeric copolymer of claim 18, comprising less than 1 wt. % C) vinyl aromatic monomer, wherein the amount of B) conjugated diene monomer is 95 to 99.95 wt. %, by weight of the copolymer.

23. The elastomeric copolymer of any of claim 18, wherein the conjugated diene monomer is selected from 1,3-butadiene, isoprene, 1,3-pentadiene, 2,3-dimethyl-1,3-butadiene, 2-methyl-1,3-pentadiene, 2,3-dimethyl-1,3-pentadiene, 2-phenyl-1,3-butadiene, and 4,5-diethyl-1,3-octadiene.

24. The elastomeric copolymer of claim 18, wherein the copolymer comprises units having a linear structure.

25. The elastomeric copolymer of claim 18, wherein the copolymer comprises units having a branched structure.

26. The elastomeric copolymer of claim 18, wherein the copolymer comprises units having a star structure and being produced by the reaction of metal-terminated living linear copolymer with one or more coupling agents in anionic polymerization conditions.

27. A method for producing a rubber comprising vulcanizing the elastomeric copolymer according to claim 18 in the presence of one or more vulcanizing agents.

28. A rubber as obtainable according to the method of claim 27.

29. A rubber composition comprising x) a rubber component comprising the rubber according to claim 28.

30. The rubber composition according to claim 29, further comprising y) one or more fillers, wherein the amount of filler coponent y) is 10 to 150 parts by mass relative to 100 parts by mass of the rubber component x) (phr).

31. The rubber composition according to claim 29, wherein the rubber component x) also comprises one or more further rubbery polymers.

32. A tire component comprising the rubber composition of claim 31.

33. A tire comprising the tire component of claim 32.

34. The functionalized conjugated diene of claim 2, wherein the terpene is selected from myrcene and ocimene.

35. The functionalized conjugated diene of claim 5, wherein each $R^5$ is the same and represents a linear or branched alkyl, aryl, or alkaryl group.

36. The functionalized conjugated diene of claim 35, wherein each $R^5$ is the same and represents $CH_3$ or $C_6H_5$.

37. The method of claim 10, wherein the vinyl aromatic monomer is selected from styrene, 1-vinylnaphthalene, 3-methylstryene, 3,5-diethylstryene, 4-propylstyrene, 2,4,6-trimethylstyrene, 4-dodecylstyrene, 3-methyl-5-n-hexylstyrene, 4-propylstyrene, 2,4,6-trimethylstyrene, 4-dodecylstyrene, 3-methyl-5-n-hexylstyrene, 4-phenylstyrene, 2-ethyl-4-bensylstyrene, 3,5-diphenylstyrene, 2,3,4,5-tetraethylstyrene, 3-ethyl-1-vinylnaphthalene, 6-isopropyl-1-vinylnaphthalene, 6-cyclohexyl-1-vinylnaphthalene, 7-dodecyl-2-vinylnaphthalene, and α-methylstyrene.

38. The method of claim 11, wherein the amount of the one or more functionalized conjugated dienes is in a range of form 0.2 to 0.8 wt. %, based on the weight of the elastomeric copolymer.

39. The process of claim 16, wherein the metal chloride 1) is selected from chlorides of one or more of Ni, Co, Ti, Nd, V, Ti, Zr, and Fe, and the co-catalyst 2) is selected from one or more of aluminium and magnesium alkyl compounds.

40. The process of claim 17, wherein the non-halide metal compound 1) is one or more Nd compounds.

41. The elastomeric copolymer of claim 19, wherein the amount of B) conjugated diene monomer is 65 to 80 wt. %, by weight of the copolymer.

42. The elastomeric copolymer of claim 21, wherein the amount of C) vinyl aromatic monomer is 20to 35 wt .%, by weight of the copolymer.

43. The elastomeric copolymer of claim 22, comprising no C) vinyl aromatic monomer, wherien the amount of B) conjugated diene monomer is 99.0to 99.4 wt. %, by weight of the copolymer.

44. The elastomeric copolymer of claim 26, wherein a.:
I) the coupling agent is a tin halide coupling agent, or
II) the coupling agent is a silicon halide coupling agent, and/or wherein b. the fraction of units having star structure is between 0and 75%, by weight of the copolymer.

45. The elastomeric copolymer of claim 44, wherein the a. I), the tin halide coupling agent is tin tetrachloride.

46. The elastomeric copolymer of claim 44, wherein in a. II), the silicon halide coupling agent is selected form silicon tetrachloride, silicon tetrabromide, silicon tetrafluoride, silicon tetraiodide, hexachlorodisilane, hexabromodisilane, hexafluorodisilane, hexaiododisilane, octachlorotrisilane, octabromotrisilane, octafluorotrisilane, octaiodorisilane, hexachlorodisiloxane, 2,2,4,4,6,6-hexachloro-2,4,6-trililapheptane-1,2,3,4,5,6-hexakis[2(methyldichlorosilyl)ethyl]benzene, and alkyl silicon halides of general formula (V)

wherein $R^6$ is a monovalent aliphatic hydrocarbon group haivng 1 to 20 carbon atoms or a monovalent aromatic hydrocarbon group having 6 to 18 carbon atoms; n is an integer of 1 to 2; and X can be a chlorine, bromine, fluorine or iodine atom.

47. The rubber composition according to claim 29, further comprising y) one or more fillers.

48. The rubber compositioin according to claim 47, wherein the filler is selected from the group consisting of silica, carbon black, and mixtures thereof.

49. The rubber composition according to claim 30, wherein the amount of filler component y) is 30 to 130 phr.

50. The rubber composition according to claim 31, wherein the further rubbery polymer is selected from the group consisting of natural rubber, synthetic isoprene rubber, butadiene rubber, styrene-butadiene rubber, ethylene-α-olefin copolymer rubber, ethylene-α-olefin-diene copolymer rubber, acrylonitrile-butadiene copolymer rubbere, chloroprene rubber, and halogenated butyl rubber.

51. The tire component of claim 32, which is a tire tread.

* * * * *